United States Patent [19]
Friedman

[11] Patent Number: 5,935,091
[45] Date of Patent: Aug. 10, 1999

[54] HAEMOSTATIC CIRCUMCISION BANDAGE

[76] Inventor: Jack Friedman, 5050 Bourret, #209, Montreal Que., Canada, H3W1L4

[21] Appl. No.: 08/993,095

[22] Filed: Dec. 18, 1997

[51] Int. Cl.⁶ ..................................................... A61F 13/00
[52] U.S. Cl. ................................ 602/79; 602/41; 602/58; 602/67; 128/844; 2/21; 604/37
[58] Field of Search ........................... 602/41, 79; 604/37

[56] References Cited

U.S. PATENT DOCUMENTS

| | | | |
|---|---|---|---|
| 5,183,460 | 2/1993 | Scherz ........................................ | 602/79 |
| 5,409,472 | 4/1995 | Rawlings et al. ......................... | 604/37 |

OTHER PUBLICATIONS

3M Microfoam, Ordering Info with cover page.

*Primary Examiner*—Jerome Donnelly
*Assistant Examiner*—Kelvin Hart
*Attorney, Agent, or Firm*—Mila Shvartsman

[57] ABSTRACT

The present invention relates to a haemostatic circumcision bandage comprising a bandage body made of a pliable waterproof material and of a unitary configuration. The bandage has a shaft supporting portion adapted to be wrapped around an entire penile shaft protecting it against contamination and a body attachment portion connected to the shaft supporting portion, which is adapted to be temporarily attached to a wearer's body and provided to keep the bandage in place. The bandage also has a resilient pad placed on the shaft supporting portion, which is adapted to facilitate haemostasis by means of applying a gentle even compression, as well as an absorbent pad placed over the resilient pad, which is provided to help absorb blood and promote healing a wound caused by circumcision. The body attachment portion further comprises a central portion adapted to be attached to a scrotum area and two symmetrical wing portions located on both sides of the central portion and adapted to be attached to the abdomen and inguinal areas. The shaft supporting portion further comprises a tab portion provided for easy removal of the bandage, and the resilient pad is made of rubber foam or sponge.

7 Claims, 1 Drawing Sheet

HAEMOSTATIC CIRCUMCISION BANDAGE

The present invention is related to bandages, and more particularly to a haemostatic circumcision bandage.

Currently, most known bandages applied after circumcision of a male infant are in the form of long strips of iodoform or Vaseline gauze which are wrapped around the penis and sometimes tied to stay in place. Alternatively, some dressings consist of a small piece of plain gauze smeared with antibiotic cream and fastened with adhesive tape, or not secured at all. Topical coagulant agents such as OXYCEL or SURGICEL are occasionally used and applied to the wound. Powders like Bismuth Subgalate and the like are also sprinkled on the dressings if excessive oozing of blood is noted.

The known dressing have the following problems:

- they are messy, time consuming to prepare and difficult to keep in place because of the lubricant nature of creams and ointment; thus, they can easily slide off the penis, especially if it is short;
- conversely they may be difficult to remove especially if a lot of adhesive tape is applied or the tissues stick to the adhesive material;
- they may be so tightly wound that they can jeopardize the blood circulation to the gland, cause soft tissue swelling or interfere with urination. As a result, they require careful supervision after application, sometimes requiring loosening or completely changing of the bandage;
- they can become so soiled with urine and faecal matter that their protective function is diminished and they may need replacement;
- powdered haemostatic agents are often applied on top of the dressing rather than against the wound itself where it is needed the most The bandage in the present invention addresses these problems and seeks to minimize them.

SUMMARY OF THE INVENTION

Broadly, the present invention relates to a haemostatic circumcision bandage comprising:

- a bandage body made of a pliable waterproof material having
- a shaft supporting portion adapted to be wrapped around an entire penile shaft protecting said shaft against contamination;
- a body attachment portion connected to said shaft supporting portion, said body attachment portion is adapted to be temporarily attached to a wearer's body and provided to keep said bandage in place;
- a resilient pad placed on said shaft supporting portion, said resilient pad is adapted to facilitate haemostasis by means of applying a gentle even compression;
- an absorbent pad placed over said resilient pad, said absorbent pad is provided for helping absorb blood and promote healing a wound caused by circumcision. Said bandage body has a unitary configuration.

In another embodiment of the present invention, said body attachment portion further comprises:

- a central portion adapted to be attached to a scrotum area and
- two symmetrical wing portions located on both sides of said central portion and adapted to be attached to an abdomen and inguinal areas. Said shaft supporting portion further comprises a tab portion provided for easy removal of said bandage, and said resilient pad is made of rubber foam or sponge.

In yet another embodiment, said absorbent pad comprises a non-adherent gauze impregnated with a contact coagulant agent, and said bandage is affixed to a protective liner or backing having a shape corresponding to the shape of said bandage.

DETAILED DESCRIPTION OF THE PREFERRED EMBODIMENT

Figure 1:
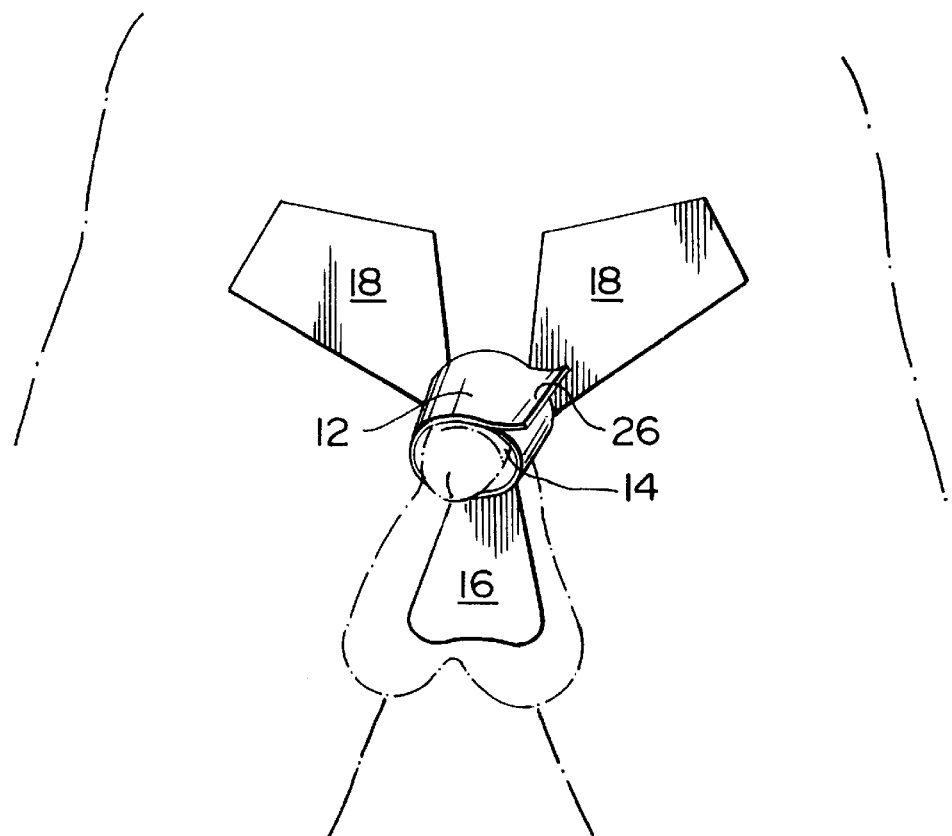
FIG. 1 shows a perspective view of the haemostatic circumcision bandage of the present invention in use.
Figure 2:
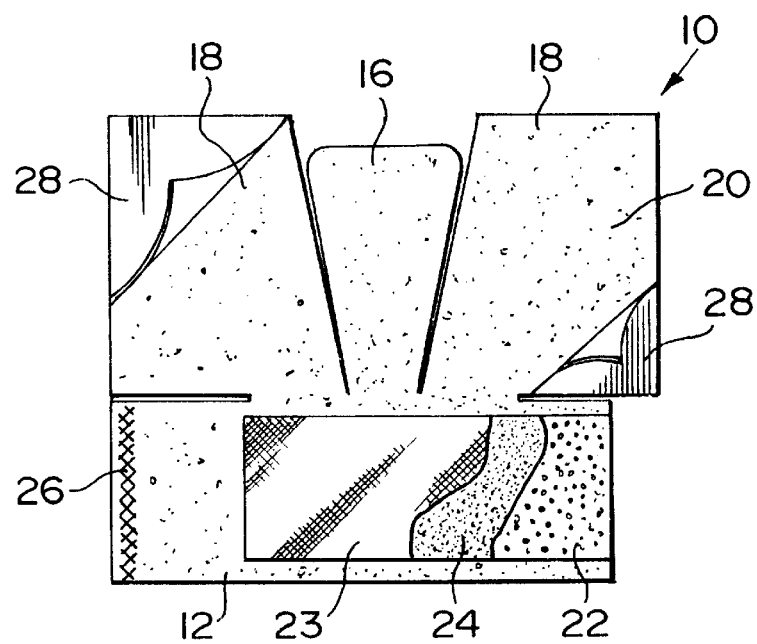
FIG. 2 shows a back view of the bandage of FIG. 1.

Referring to drawings, FIGS. 1 and 2 show a bandage 10 comprising a shaft supporting portion 12 made of pliable waterproof material, which is adapted to be wrapped around the penis shaft 14 after circumcision. Bandage 10 is temporarily attached to the wearer's body by means of a body attachment portion consisting of two symmetrical right and left wing portions 18 provided to be attached to the abdomen and inguinal areas of the wearer and by means of a central portion 16 attached to the scrotum below. Shaft supporting portion 12 and body attachment portions 16 and 18 form a unitary configuration, wherein an inner surface 20 is made of waterproof adhesive and an outer surface of waterproof material, such as plastic. Preferably, central portion 16 and right and left portions 18 have a shape of a bird's tail, which in use opens to follow the contours of the wearer's body. The inner surface of the shaft supporting portion 12 is provided with permanently attached assembly comprising a resilient pad 22 and an absorbent pad 24 placed over pad 22. The purpose of resilient pad 22 is to facilitate haemostasis by means of applying an even compression around the shaft 14 without causing an undesirable interference with urination or blood supply to the gland. Resilient pad 22 could be made of ⅒ inch layer of sponge, foam or other similar material. Absorbent pad 24 is provided to help heal the wound caused by circumcision and comprises 1/16 inch gauze layer of absorbent material which can be impregnated with a topical clotting agent such as Bismuth Subgalate or the like. Layer 23 represents a very thin perforated plastic mesh to prevent the sticking of wound to gauze below.

That support portion 12 is also provided with a ¼ inch non-adhesive tab 26 to facilitate the easy removal of the bandage. The bandage 10 can be trimmed to the size of the wearer and be tightened as required. This bandage 10 can remain in place for 24–48 hours without interfering with normal urination. If desired, a topical anti-biotic ointment can be also applied to the wound. The entire bandage is stuck to a peel-off backing or liner 28 of smooth plastic divided into segments corresponding to the shape of the bandage 10 to facilitate removal of the bandage prior to use. In use the bandage should be applied by affixing the scrotal portion 16 first, then the shaft supporting portion 12 is wrapped around penile shaft, and finally the two symmetrical wing portions 18 are stuck to the thighs and lower abdomen.

Although the haemostatic circumcision bandage 10 of the present invention is designed for the newborn specifically, it can be changed in size for use in other situations.

Suggested topical clotting agents for possible use with the present invention are the following compositions:

bismuth subgalate, calcium or sodium alginate, SURGICEL, kaltostat, aluminum sulphate, extrait titre de centella asiatica 2 gm, exipient QSP 100 gm.

Besides, the absorbent layer of the gauze can also be impregnated with a topical anesthetic or even a topical antibiotic so that nothing has to be added by the user.

When using the bandage according to the present invention, the following trouble-shooting guide should be considered:

- too tight application of the bandage may still restrict the blood circulation to the gland. The user should check for urination capacity from 4–6 hours after application of the bandage. Colour of the penile tip can also be assessed;
- if skin is dirty or not dry enough prior to the application of the bandage, the adhesion may be insufficient. It is suggested to clean and dry the skin with soft paper towels or a blow dryer prior to the application of the bandage;
- if penis is very short, the pad may not grip properly. In this case the gland may sink into the dressing so that no compression is applied to the shaft;
- bleeding may be so severe that no simple dressing can arrest it. In this case minor surgery or cauterization may be required.

The present invention has the following advantages:

- application is a simple one step procedure in which the entire shaft of the penis is covered to minimize the risk of contamination and infection; it is held securely in place by adhesive strips to the body of the wearer;
- easy maintenance of applied bandage: urine and faecal matter will not penetrate inside the shaft portion as with gauze;
- haemostasis is facilitated by means of applying a gentle and even compression to the shaft while permitting normal blood supply to the gland and normal urination; in addition, a topical coagulant agent is held directly against the bleeding site;
- the bandage is open at the tip permitting easy visualization of the gland and proper urination;
- easy removal of the bandage or opening it to re-adjust tension with a small non-stick tab;
- requires less supervision and may not need more than a single application for the wound if it stays in place for 2–3 days;
- can be removed by an ordinary person without use of scissors;
- a well fitted bandage would also help keep urine and faecal matter off and result in less irritation to the patient.

Thus, it can be seen that the objects of the present invention have been satisfied by the structure presented hereinabove. While in accordance with the Patent Statutes, only the best mode and preferred embodiments of the present invention have been presented and described in detail it is to be understood that the invention is not limited thereto or thereby. Accordingly, for an appreciation of the true scope and breadth of the invention, references should be made to the following claims.

I claim:

1. Haemostatic circumcision bandage comprising a bandage body made of a pliable waterproof material having a shaft supporting portion adapted to be wrapped around an entire penile shaft;

a body attachment portion connected to said shaft supporting portion, said body attachment portion is adapted to be temporarily attached to a wearer's body and provided to securely keep said bandage in place;

wherein said shaft supporting portion has an integrated configuration comprising a permanently attached assembly including:

a resilient pad placed on said shaft supporting portion, said resilient pad is adapted to facilitate haemostasis of a wound caused by circumcision by means of applying an even compression to said penile shaft throughout the time of application of said bandage;

an absorbent pad placed over said resilient pad, said absorbent pad is provided for helping absorb blood, promote healing and to maintain dryness of the wound, wherein said body attachment portion further comprises:

a central portion extending perpendicularly from substantially a middle of said shaft supporting portion, said central portion is adapted to be attached to a scrotum area and two symmetrical wing portions located on both sides of said central portion, said wing portions being spread between said central portion and said shaft supporting portion in such a way that lateral edges of said wings adjacent to said central portion are substantially parallel to the corresponding adjacent lateral edges of said central portion, said central portion is smaller in permeter and decreases in diameter moving from the outer edge toward the shaft supporting portion, said wing portions are constructed in an angular fashion in such a way that the lateral edges of said wings adjacent to said shaft supporting portion are substantially parallel to the corresponding adjacent edges of said shaft supporting portion and have slits to separate them from said shaft supporting portion in order to allow the enhanced placement of the bandage on the body and scrotum.

2. Haemostatic circumcision bandage according to claim 1, wherein said bandage body has a unitary configuration.

3. Haemostatic circumcision bandage according to claim 1, wherein said central portion has a configuration of a bird's tail.

4. Haemostatic circumcision bandage according to claim 1, wherein said shaft supporting portion further comprises a tab portion provided for easy removal of said bandage.

5. Haemostatic circumcision bandage according to claim 1, wherein said resilient pad is made of rubber foam or sponge.

6. Haemostatic circumcision bandage according to claim 1, wherein said absorbent pad comprises a non-adherent gauze impregnated with a contact coagulant agent, wherein said gauze is covered by a fine plastic mesh provided to limit adhesion of said gauze to the wound.

7. Haemostatic circumcision bandage according to claim 1, wherein said bandage is affixed to a protective liner or backing having a shape corresponding to the shape of said bandage.

\* \* \* \* \*